US011926814B2

(12) United States Patent
Rogers et al.

(10) Patent No.: US 11,926,814 B2
(45) Date of Patent: Mar. 12, 2024

(54) MULTI-CHAMBER FLUIDIC PLATFORM

(71) Applicant: Northwestern University, Evanston, IL (US)

(72) Inventors: Hunter B. Rogers, Evanston, IL (US); Teresa K. Woodruff, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/640,996

(22) PCT Filed: Aug. 21, 2018

(86) PCT No.: PCT/US2018/047210
§ 371 (c)(1),
(2) Date: Feb. 21, 2020

(87) PCT Pub. No.: WO2019/040423
PCT Pub. Date: Feb. 28, 2019

(65) Prior Publication Data
US 2020/0224147 A1    Jul. 16, 2020

Related U.S. Application Data

(60) Provisional application No. 62/549,213, filed on Aug. 23, 2017.

(51) Int. Cl.
C12M 1/36 (2006.01)
C12M 1/00 (2006.01)
C12M 1/24 (2006.01)
C12M 3/00 (2006.01)
C12M 3/06 (2006.01)

(52) U.S. Cl.
CPC ............ *C12M 41/48* (2013.01); *C12M 23/08* (2013.01); *C12M 23/16* (2013.01); *C12M 23/22* (2013.01); *C12M 23/42* (2013.01)

(58) Field of Classification Search
None
See application file for complete search history.

(56) References Cited

U.S. PATENT DOCUMENTS

| 6,021,800 A | 2/2000 | Schild |
| 6,132,685 A | 10/2000 | Kercso |
| 9,695,399 B2 | 7/2017 | Woodruff |

(Continued)

FOREIGN PATENT DOCUMENTS

| EP | 2245453 B1 | 10/2016 |
| WO | 2016064838 A1 | 4/2016 |
| WO | 2016179664 A1 | 11/2016 |

OTHER PUBLICATIONS

Busek et al., Characterization and simulation of peristaltic micropumps, 2013, J. Sens. Sens. Syst., 2, 165-169 (Year: 2013).*

(Continued)

*Primary Examiner* — Holly Kipouros
(74) *Attorney, Agent, or Firm* — Quarles & Brady LLP

(57) ABSTRACT

Provided herein are systems comprising multiple fluidically-coupled chamber volumes. In particular, provided herein are cell culture systems that incorporate fluid flow between multiple cell culture volumes, and method of use thereof for the culture of multiple related cell/tissue types.

15 Claims, 12 Drawing Sheets

(56) References Cited

U.S. PATENT DOCUMENTS

| | | | |
|---|---|---|---|
| 2003/0039591 A1* | 2/2003 | Pham | B01L 3/50855 422/561 |
| 2007/0092958 A1* | 4/2007 | Syed | C12N 5/0619 435/173.8 |
| 2008/0047836 A1* | 2/2008 | Strand | B01L 3/502715 204/644 |
| 2010/0015697 A1* | 1/2010 | Junger | C12M 21/06 435/307.1 |
| 2010/0285558 A1 | 11/2010 | Wu | |
| 2011/0183312 A1* | 7/2011 | Huang | C12M 23/16 435/286.5 |
| 2012/0034695 A1 | 2/2012 | Sethu | |
| 2013/0143230 A1* | 6/2013 | Tolias | G01N 33/5008 435/7.1 |
| 2014/0099705 A1 | 4/2014 | Hung | |
| 2014/0142000 A1* | 5/2014 | Tung | C12M 41/32 506/40 |
| 2014/0212964 A1* | 7/2014 | Cuiffi | C12M 29/00 435/325 |
| 2014/0315325 A1* | 10/2014 | Cobb | B01L 3/50825 436/174 |
| 2015/0329816 A1* | 11/2015 | Owens | C12M 23/04 435/298.2 |
| 2016/0340632 A1* | 11/2016 | Breinlinger | C12M 23/34 |
| 2017/0067009 A1* | 3/2017 | Sloane | C12N 5/0062 |
| 2018/0272340 A1* | 9/2018 | Govyadinov | B01L 3/502707 |

OTHER PUBLICATIONS

Tsamandouras et al., Integrated Gut and Liver Microphysiological Systems for Quantitative In Vitro Pharmacokinetic Studies, published online Jul. 27, 2017, The AAPS Journal (Year: 2017).*

Corning, Transwell Permeable Supports, 2012 (Year: 2012).*

International Searching Authority, International Search Report and Written Opinion for application PCT/US2018/047210, dated Oct. 26, 2018.

Reichen, M. et al. "Development of a multiplexed microfluidic platform for the automated cultivation of embryonic stem cells." Journal of laboratory automation 18.6 (2013): 519-529.

Kiao, S, et al. "A microfluidic culture model of the human reproductive tract and 28-day menstrual cycle." Nature communications 8 (2017): 14584.

* cited by examiner

MULTI-CHAMBER FLUIDIC PLATFORM

CROSS-REFERENCE TO RELATED APPLICATIONS

The present application is the U.S. national stage entry of international application PCT/US2018/047210, filed Aug. 21, 2018, which claims the benefit U.S. Provisional Application 62/549,213, filed Aug. 23, 2017, the contents of which are incorporated herein by reference in their entireties.

STATEMENT REGARDING FEDERALLY SPONSORED RESEARCH

This invention was made with government support under TR001207 awarded by the National Institutes of Health. The government has certain rights in the invention.

BACKGROUND

A variety of cell culture devices and systems are known in the field. However, none are capable of simultaneously accommodating multiple cell/tissue types, in a format-agnostic manner, in a platform that contains the necessary components to control the desired amount of flow between separate chambers of the platform, and all contained within dimensions of a standard microplate to enable use of the platform with common hardware and instruments.

SUMMARY OF THE DISCLOSURE

Provided herein are systems comprising multiple fluidically-coupled chamber volumes. In particular, provided herein are cell culture systems that incorporate fluid flow between multiple cell culture volumes, and method of use thereof for the culture of multiple related cell/tissue types.

In some embodiments, provided herein are tissue culture platforms having standard microplate dimensions and comprising: a first plate, a second plate opposed to and engaging the first plate to form an enclosed volume therebetween, a plurality of chambers coupled to at least one of the first plate or the second plate and enclosed within the enclosed volume, a plurality of channels enclosed within the enclosed volume and connecting the plurality of chambers to allow flow of media therebetween, and at least one pump enclosed within the enclosed volume, wherein the at least one pump facilitates the flow of media between the plurality of chambers and regulates a directionality of the flow of media between the plurality of chambers.

In some embodiments, two or more of the plurality of chambers are culture chambers, each of the culture chambers configured to contain a volume of culture media and cells, wherein each culture chamber comprises an inlet port and an outlet port each configured to allow the flow of media between the culture chambers while preventing movement of the cells between the culture chambers. In some embodiments, the plurality of chambers includes at least one donor chamber configured to contain a volume of culture media, wherein the at least one donor chamber comprises an outlet port configured to allow the flow of media from the at least one donor chamber to one or more of the plurality of chambers via one or more of the plurality of channels and facilitated by the at least one pump. In some embodiments, the plurality of chambers includes at least one waste chamber configured to contain a volume of culture media, wherein the at least one waste chamber comprises an inlet port configured to receive media from one or more of the plurality of chambers via one or more of the plurality of channels and facilitated by the at least one pump.

In some embodiments, the first plate comprises exterior walls extending away from a base of the first plate such that the exterior walls engage with the second plate to form the enclosed volume. In some embodiments, the first plate comprises a plurality of recesses formed therein that couple the plurality of chambers to the first plate.

In some embodiments, the channels comprise sections of tubing. In some other embodiments, the channels comprise microfluidic channels formed in the first plate.

In some embodiments, the plurality of chambers are selectively connected by the plurality of channels to create a desired media flow-path through and between the plurality of chambers. In some embodiments, the at least one pump is positioned along one of the plurality of channels connecting a pair of the plurality of chambers. In some embodiments, the at least one pump facilitates unidirectional flow between the pair of the plurality of chambers.

In some embodiments, the tissue culture platforms further comprise a microcontroller that is electronically linked to the at least one pump and controls the flow of media through the plurality of chambers, the plurality of channels, and the at least one pump. In some embodiments, the tissue culture platforms further comprise a power source connected to at least one of the microcontroller or the at least one pump. In some embodiments, the power source is a battery enclosed within the enclosed volume. In some embodiments, the power source is located externally to the enclosed volume. In some embodiments, the power source is an external power source that can be a battery, an AC power source, a DC power source, a USB connection, and so on.

In some embodiments, at least one of the first plate or the second plate comprises one or more openings to allow access to the enclosed volume when the first plate is engaged with the second plate. In some embodiments, at least one of the first plate or the second plate comprises one or more transparent portions to provide visual access to one or more of the plurality of chambers. In some embodiments, visual access allows quantitative and/or qualitative assessment of contents of one or more of the plurality of chambers.

In some embodiments, at least two (e.g., 2, 3, 4, 5, 6, or more) of the plurality of chambers are fabricated as a one-piece unit. In some embodiments, at least two (e.g., 2, 3, 4, 5, 6, 7, 8, 9, 10, or more) of the plurality of chambers are fabricated as separate units.

In some embodiments, provided herein are tissue culture platforms having standard microplate dimensions and comprising: a first plate, a second plate opposed to and engaging the first plate to form an enclosed volume therebetween, a plurality of chambers coupled to at least one of the first plate or the second plate and enclosed within the enclosed volume, a plurality of channels enclosed within the enclosed volume and connecting the plurality of chambers to facilitate flow of media therebetween, and at least one pump enclosed within the enclosed volume, wherein the at least one pump regulates a rate and a directionality of the flow of media through the plurality of channels. The plurality of chambers comprises a donor chamber, a first culture chamber, a second culture chamber, and a waste chamber. The donor chamber is configured to contain a volume of culture media, wherein the donor chamber comprises an outlet port configured to allow flow of media from the donor chamber via a first segment of the channels. The first culture chamber is configured to contain a volume of culture media and cells, wherein the first culture chamber comprises an inlet port connected to or aligned with the first segment of the channels and configured to receive media from the donor chamber, wherein the first culture chamber comprises an outlet port connected to or aligned with a second segment of the channels and configured to allow flow of media from the first culture chamber via the second segment of the channels, wherein at least one of the inlet port or the outlet port of the first culture chamber is configured to prevent movement of cells from the first culture chamber. The second culture chamber is configured to contain a volume of culture media and cells, wherein the second culture chamber comprises an inlet port connected to or aligned with the second segment of the channels and configured to receive media from the first culture chamber, wherein the second culture chamber comprises an outlet port connected to or aligned with a third segment of the channels and configured to allow flow of media from the second culture chamber via the third segment of the channels, wherein at least one of the inlet port or the outlet port of the second culture chamber is configured to prevent movement of cells from the second culture chamber. The waste chamber is configured to contain a volume of culture media, wherein the waste chamber comprises an inlet port configured to receive media at least one of directly or indirectly from the third segment of the channels.

In some embodiments, the at least one pump comprises a plurality of pumps and at least one of the plurality of pumps is located along each of the first, second, and third segments of the channels.

In some embodiments, the second culture chamber further comprises a second outlet port and the first culture chamber further comprises a second inlet port, wherein the second outlet port of the second culture chamber and the second inlet port of the first culture chamber are connected by a fourth segment of the channels configured to facilitate the flow of media from the second culture chamber to the first culture chamber, wherein the second outlet port of the second culture chamber and/or the second inlet port of the first culture chamber are configured to prevent the movement of cells through the fourth segment of the channels. In some embodiments, the at least one pump is located along the fourth segment of the channels. In some embodiments, the inlet port of the waste chamber is connected to or aligned with the third segment of the channels, and the waste chamber receives flow of media directly from the second culture chamber.

In some embodiments, the plurality of chambers further comprises a third culture chamber configured to contain a volume of culture media and cells, wherein the third culture chamber comprises an inlet port connected to or aligned with the third segment of the channels and configured to receive media from the second culture chamber, wherein the third culture chamber comprises an outlet port connected to or aligned with an additional segment of the channels and configured to allow flow of media from the third culture chamber via the additional segment of the channels, wherein at least one of the inlet port or outlet port of the third culture chamber is configured to prevent the movement of cells from the third culture chamber. In some embodiments, the inlet port of the waste chamber is connected to or aligned with the additional segment of the channels, and the waste chamber receives flow of media directly from the third culture chamber.

In some embodiments, the plurality of chambers further comprises one or more additional culture chambers, each additional culture chamber configured to contain a volume of culture media and cells, wherein each additional culture chamber comprises an inlet port connected to or aligned with a segment of the channels and configured to receive media, and an outlet port connected to or aligned with a segment of the channels and configured to allow flow of media from the additional culture chamber, wherein at least one of the inlet port or the outlet port of each of the additional culture chambers is configured to prevent the movement of cells from the that additional culture chamber.

In some embodiments, the at least one pump facilitates unidirectional flow through the segment of the channels with which the at least one pump is associated.

In some embodiments, the donor and waste chambers are fabricated as a single piece. In some embodiments, each of the culture chambers are fabricated as separate units.

In some embodiments, provided herein are tissue culture systems comprising: (a) a tissue culture platform described herein; (b) culture media within the donor chamber, first culture chamber, and second culture chamber; (c) a first cell population within the first culture chamber; and (d) a second cell population within the second culture chamber. In some embodiments, the cell populations are tissue explants, 3D cell culture, 2D cell culture, or any other suitable cell/tissue culture format.

In some embodiments, provided herein are tissue culture systems comprising: (a) a tissue culture platform described herein; (b) culture media within the donor chamber, first culture chamber, second culture chamber, and third culture chamber; (c) a first cell population within the first culture chamber; (d) a second cell population within the second culture chamber; and (e) a third cell population within the third culture chamber.

In some embodiments, provided herein are tissue culture systems comprising: (a) a tissue culture platform described herein; (b) culture media with the donor chamber, first culture chamber, second culture chamber, third culture chamber, and additional culture chambers; (c) a first cell population within the first culture chamber; (d) a second cell population within the second culture chamber; (e) a third cell population within the third culture chamber; and (f) additional cell populations within the additional culture chambers.

In some embodiments, each of the cell populations with the tissue culture systems herein comprise the same cell type. In some embodiments, each of the cell populations with the tissue culture systems herein different cell types. In some embodiments, the tissue culture systems herein comprise two or more cell populations of a first cell type and one or more cell populations of a second cell type.

In some embodiments, factors secreted from the first cell population flow to the second cell population. In some embodiments, factors secreted from the second cell population flow to the third cell population. In some embodiments, factors secreted from the third cell population flow to the additional cell populations.

In some embodiments, factors secreted from the second cell population flow back (via a return channel) to the first cell population. In some embodiments, factors secreted from the third cell population flow (via a return channel) back to the first and/or second cell populations.

In some embodiments, provided herein are methods of performing tissue culture (e.g., on multiple cell populations) comprising placing a tissue culture system described herein (e.g., comprising a tissue culture platform, cells, and media) under appropriate conditions to allow the growth of cells within the culture chambers. In some embodiments, the tissue culture system is placed in an instrument (e.g., shaker, incubator, etc.) configured to provide appropriate conditions for the growth of cells and configured to accept standard microplate dimensions.

In some embodiments, provided herein are methods of analyzing cells grown in tissue culture comprising placing a tissue culture system described herein in an analytical instrument configured to accept standard microplate dimensions and analyzing one or more of the cell populations with the analytical instrument. In some embodiments, the analytical instrument is selected from the group consisting of a microscope, imaging device, fluorimeter.

In some embodiments, provided herein is the use of a tissue culture system or tissue culture platform described herein in growing and/or analyzing cells. Use of a tissue culture system or tissue culture platform described herein in growing and/or analyzing cells under experimental conditions (e.g., in the presence of a drug or drug target).

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
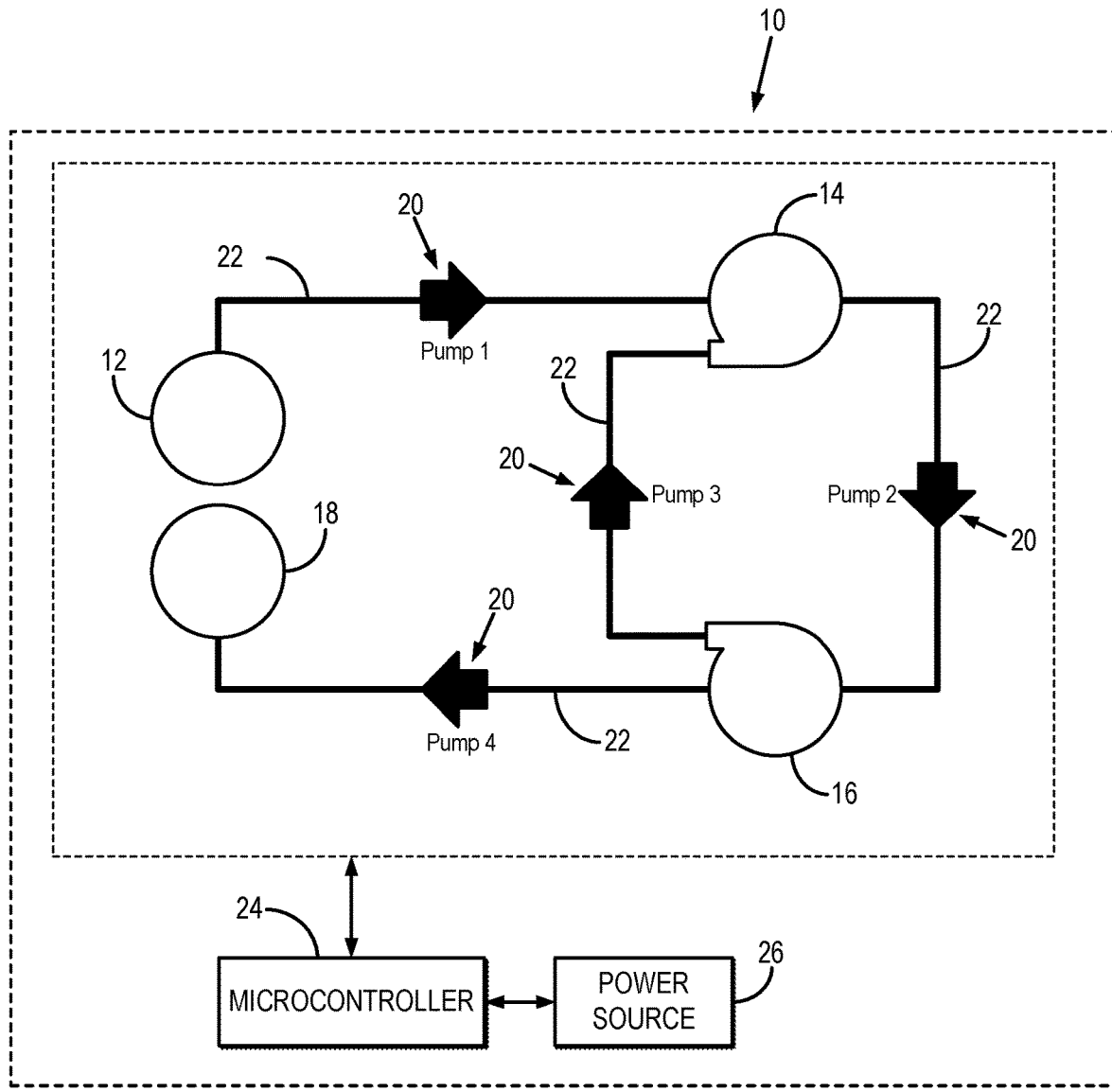
FIG. 1 is an illustration of example of a pump and flow scheme in a two-tissue system.

Although any methods and materials similar or equivalent to those described herein can be used in the practice or testing of embodiments described herein, some preferred methods, compositions, devices, and materials are described herein. However, before the present materials and methods are described, it is to be understood that the systems and methods described in the present disclosure are not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which the systems and methods described in the present disclosure belong. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a culture chamber" is a reference to one or more culture chambers and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "chamber" refers to a fully- or partially enclosed space or compartment that is capable of containing solid and/or fluid reagents/components, the flow/transfer of fluids into/out of the chamber being regulated via one or more ports. For example, the term "culture chamber" refers to an enclosed space or compartment in which cells/tissues are cultured. A "donor chamber" is a reservoir capable of holding and dispensing (via one or more ports) fluid reagents. A "waste chamber" is a reservoir capable of receiving (via one or more ports) and holding fluid reagents.

As used herein, the term "system" refers to a collection of compositions, devices, articles, materials, etc. grouped together in any suitable manner (e.g., physically associated; in fluid-, electronic-, or data-communication; packaged together; etc.) for a particular purpose.

As used herein, "standard microplate base dimensions" are width of 85.5 mm and a length of 127.8 mm.

As used herein, "standard microplate dimensions" are width of 85.5 mm, a length of 127.8 mm, and a height of 14.2 mm.

As used herein, "standard deep-well microplate dimensions" are width of 85.5 mm, a length of 127.8 mm, and a height of 21.5 mm.

The term "about" allows for a degree of variability in a value or range. As used herein, the term "about" refers to values within 10% of the recited value or range (e.g., about 50 is the equivalent of 45-55).

The term "substantially" allows for a narrow degree of variability in a value or range. As used herein, the term "substantially" refers to values within 1% of the recited value or range (e.g., substantially 50 is the equivalent of 49.5-50.5).

Provided herein are systems comprising multiple fluidically-coupled chamber volumes. In particular, provided herein are cell culture systems that incorporate fluid flow between multiple cell culture volumes, and methods of use thereof for the culture of multiple related cell/tissue types.

In some embodiments, provided herein are fluidic tissue culture systems that are compatible with standard laboratory automation hardware, including robotic handling, liquid handling, and automated imaging systems, for example, for the purpose of tissue-tissue interaction studies. Whereas traditional cell and tissue culture techniques utilize static well conditions, systems herein incorporate fluid flow between multiple chambers (e.g., donor chambers, culture chambers, waste chambers).

FIG. 1 depicts an example of a tissue culture platform 10 in accordance with some embodiments. The tissue culture platform 10 includes a donor chamber 12, a first culture chamber 14, a second culture chamber 16, and a waste chamber 18. In some embodiments, flow is facilitated by on-board pumps 20 (e.g., piezoelectric pumps) connected to culture chambers via fluidic channels 22 (e.g., tubing or microfluidic channels). In some embodiments, incorporating fluidics in this way allows for the coupling of multiple tissue constructs to create more dynamic and in-vivo-like culture conditions compared to traditional static culture. In some embodiments, the pumps 20 (e.g., piezoelectric pumps) are controlled using an on-board microcontroller 24 that is programmed to control microfluidic volumes of fluid across extended periods of culture (e.g., 1 hour, 2 hours, 4 hours, 6 hours, 8 hours, 12 hours, 16 hours, 24 hours, 2 days, 3 days, 4 days, 5 days, 6 days, 7 days, 2 weeks, 3 weeks, 4 weeks, 6 weeks, 8 weeks, 12 weeks, or more, or ranges therebetween).

In some embodiments, the tissue culture platforms 10 herein are format-agnostic, accommodating cells/tissues in cell monolayer, explant, spheroid, 3D-printed scaffold, and other formats. In some embodiments, the tissue culture platforms 10 herein comprise multi-tissue capacity. Some embodiments of the tissue culture platform 10 comprise a capacity for up to two different tissue constructs within two distinct but fluidically-connected culture modules. In other embodiments, the tissue capacity of tissue culture platforms 10 herein is two or greater (e.g., 2, 3, 4, 5, 6, 7, 8, 9, 10, or more, or ranges therein (e.g., 2-6, etc.)).

In some embodiments, the tissue culture platforms 10 herein comprise an on-board system that includes precisely-controlled pumps 20 programmed via an on-board microcontroller 24 that is powered by power source 26, which may be either an on-board battery (e.g., for wireless applications) or off-system connection (e.g., AC power source, DC power source, USB power source). The battery may be a secondary cell or rechargeable battery, including a lithium ion battery, a nickel-cadmium battery, and so on; a primary cell battery, such as an alkaline battery; or any other suitable type of battery. In some embodiments, electrical communication to the pumps 20 is provided by suitable interconnections 62, such as a pin and socket interconnection (e.g., a Molex connector) or other suitable wired or wireless connection.

In some embodiments, all components of the tissue culture platforms 10 described herein are contained within dimensions of a standard deep-well microplate (e.g., 127.8 mm×85.5 mm×21.5 mm), allowing for the tissue culture platform 10 to be used with existing hardware and instruments (e.g., robotic handling, imaging, etc.) that are compatible with standard plates (FIG. 1).

In some embodiments, the exterior dimensions of the tissue culture platforms 10 herein are the same as the dimensions of a standard microplate. Such dimensions allow the tissue culture platforms 10 to interface with laboratory and clinical hardware and instruments.

In some embodiments, a tissue culture platform 10 has standard microplate base dimensions (e.g., 85.5 mm×127.8 mm). In some embodiments, a tissue culture platform 10 has dimensions that are substantially (<1% error) those of standard microplate base dimensions. In some embodiments, a tissue culture platform 10 has dimensions that are about (<10% error) those of standard microplate base dimensions.

In some embodiments, a tissue culture platform 10 has standard microplate dimensions (e.g., 85.5 mm×127.8 mm×14.2 mm). In some embodiments, a tissue culture platform 10 has dimensions that are substantially (<1% error) those of standard microplate dimensions. In some embodiments, a tissue culture platform 10 has dimensions that are about (<10% error) those of standard microplate dimensions.

In some embodiments, a tissue culture platform 10 has standard deep-well microplate dimensions (e.g., 85.5 mm×127.8 mm×14.2 mm). In some embodiments, a tissue culture platform 10 has dimensions that are substantially (<1% error) those of standard deep-well microplate dimensions. In some embodiments, a tissue culture platform 10 has dimensions that are about (<10% error) those of standard deep-well microplate dimensions.

In some embodiments, a tissue culture platform 10 has a base that is between 110 mm and 140 mm in length (e.g., 110 mm, 112 mm, 114 mm, 116 mm, 118 mm, 120 mm, 122 mm, 124 mm, 126 mm, 128 mm, 130 mm, 132 mm, 134 mm, 136 mm, 138 mm, 140 mm, or ranges therebetween (e.g., 126-130 mm). In some embodiments, a tissue culture platform 10 has a base that is between 70 mm and 100 mm wide (e.g., 70 mm, 72 mm, 74 mm, 76 mm, 78 mm, 80 mm, 82 mm, 84 mm, 86 mm, 88 mm, 90 mm, 92 mm, 94 mm, 96 mm, 98 mm, 100 mm, or ranges therebetween (e.g., 84-88 mm). In some embodiments, a tissue culture platform 10 has a base that is between 10 mm and 30 mm in height (e.g., 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, or ranges therebetween (e.g., 13-15 mm, 21-22 mm).

Figure 2:
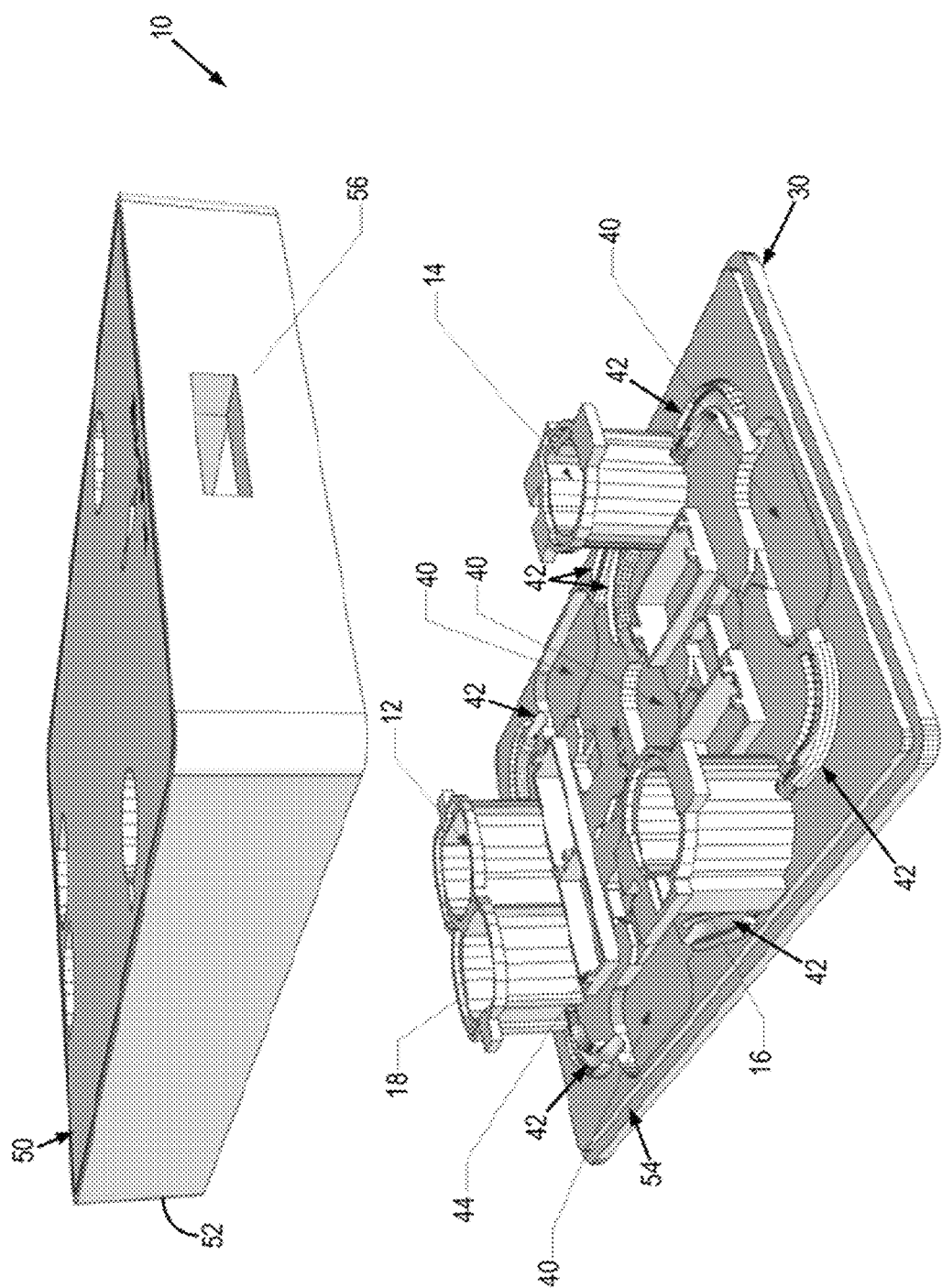
FIG. 2 is an overview of the printed parts of an example of a tissue culture platform, including the base plate, combined donor/waste module, two tissue chambers, and top plate.
Figure 3:
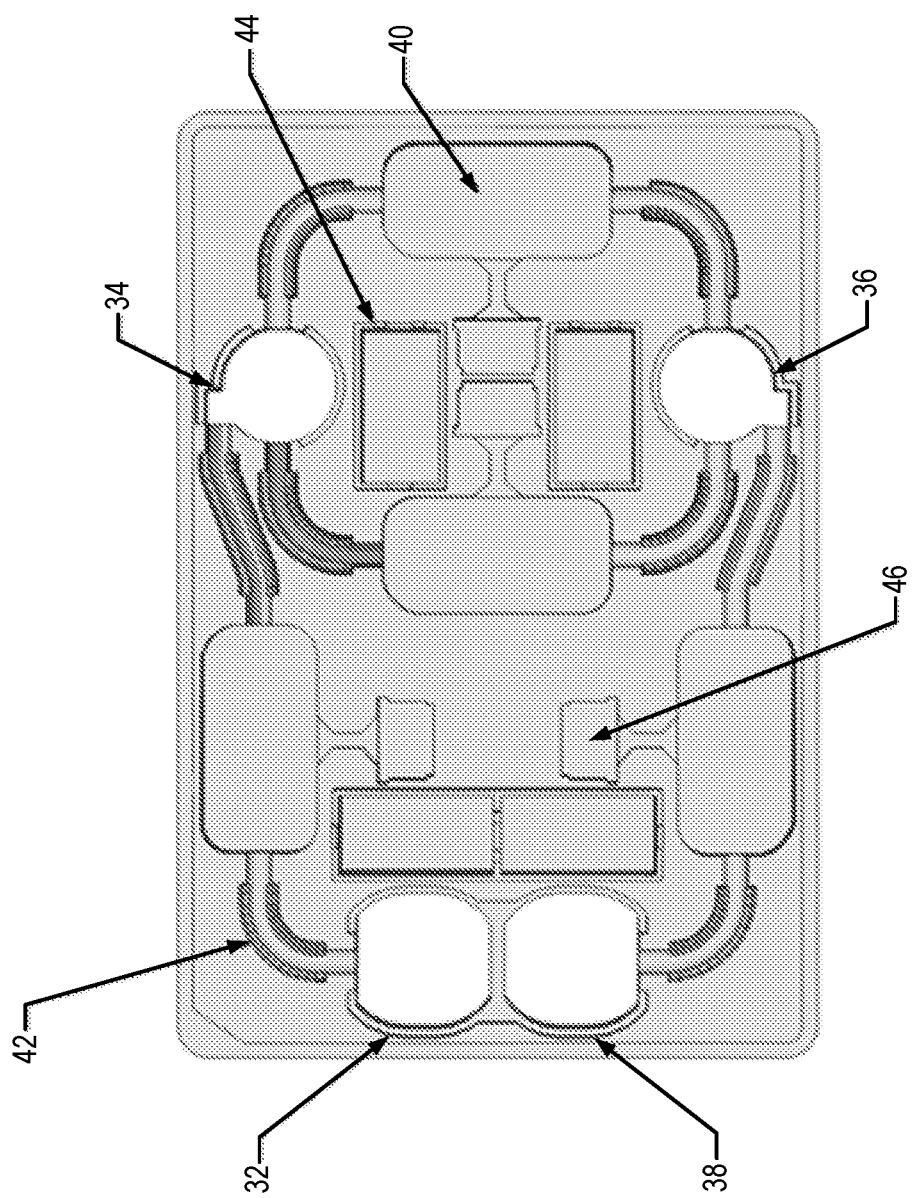
FIG. 3 is a top-down view of a bottom plate of an example of a tissue culture platform that includes fluidic channels (either printed or tubing) and recesses for modules, pumps, power connectors, and pump drivers.
Figure 4:
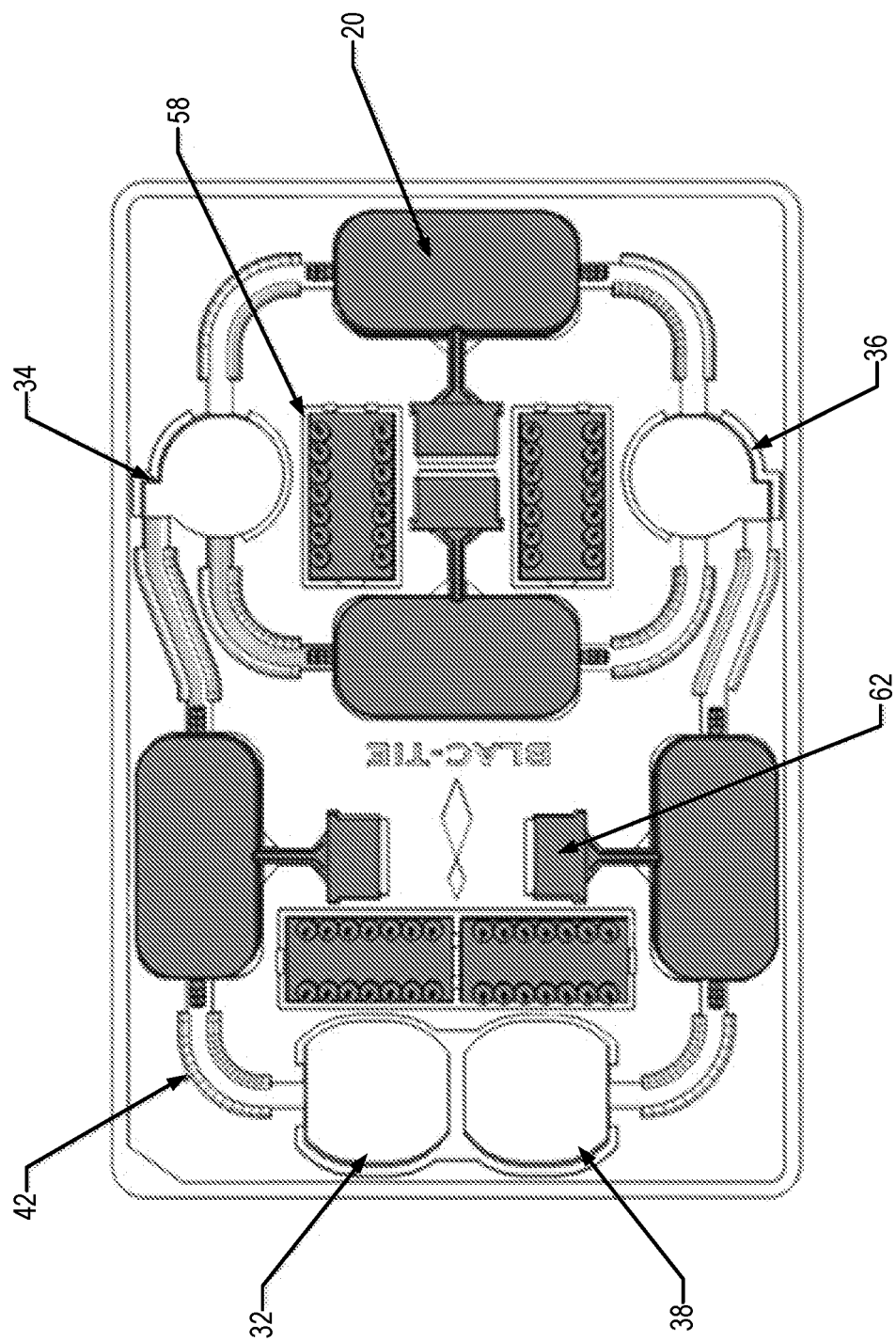
FIG. 4 is a top-down view of bottom plate of an example of a tissue culture platform that includes fluidic channels with pumps, power connectors, and pump drivers in place.
Figure 7A:
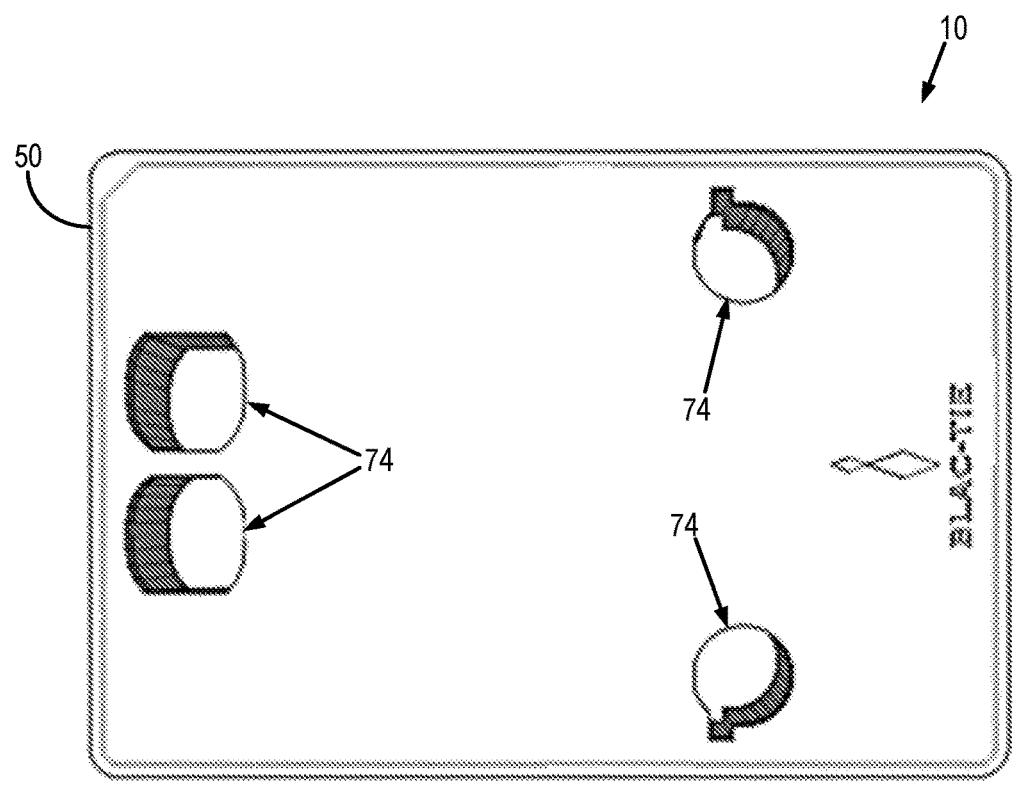
FIGS. 7A-7D show an example of assembled systems of an example tissue culture platform, viewed from: top-down (FIG. 7A), bottom-up (FIG. 7B), front-facing (FIG. 7C), and side views (FIG. 7D).
Figure 7B:
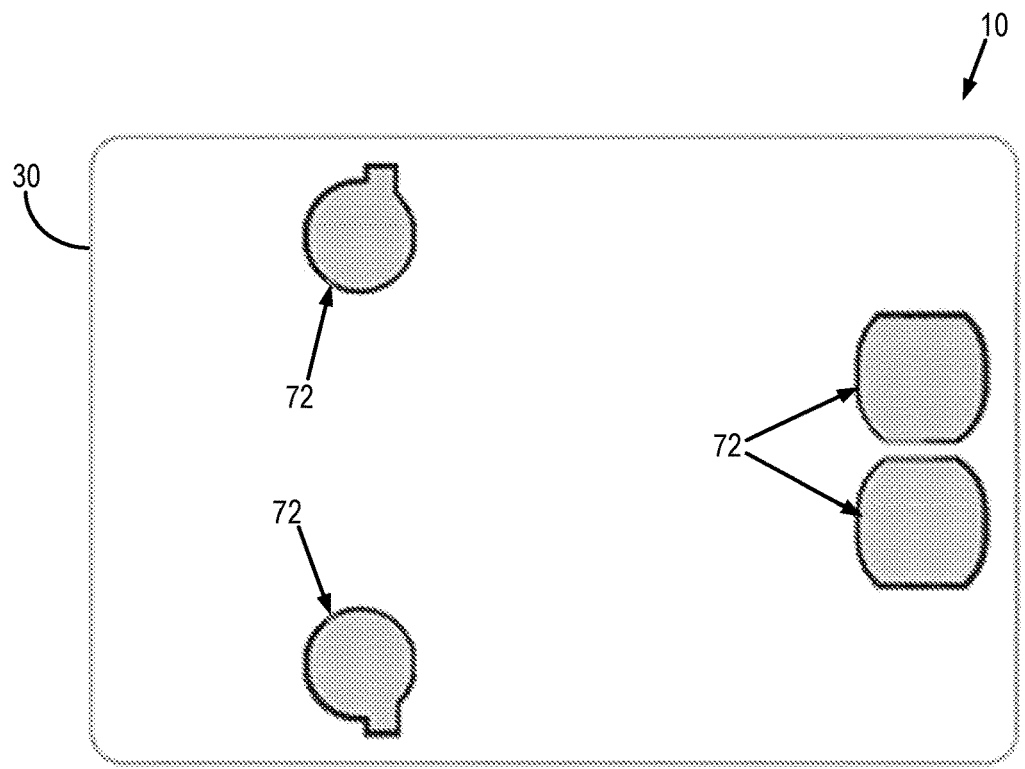

In some embodiments, a tissue culture platform 10 comprises multiple 3D printed components. An example of such a tissue culture platform 10 is shown in FIGS. 2-4. An example of a component is a bottom plate 30 (e.g., sized to have a bottom footprint of the standard microplate). In some embodiments, a bottom plate 30 comprises various recesses and/or raised portions to accommodate (and hold in place) pumps, drivers, chambers (e.g., donor, waste, culture, holding), and channels. For instance, the bottom plate can include a donor chamber recess 32, a first culture chamber recess 34, a second donor chamber recess 36, a waste chamber recess 38, pump recesses 40, channel recesses 42, and driver recesses 44, power connection recesses 46, among others. In some embodiments, as shown in FIG. 3, the bottom plate 30 comprises channel recesses 42 for channels 22 connecting the various chambers (e.g., donor chamber 12, first culture chamber 14, second culture chamber 16, waste chamber 18) or comprises microfluidic channels that connect the chambers or the recesses on the bottom plate 30 that accommodate the chambers. In some embodiments, one or more portions 72 of the bottom plate 30 (e.g., beneath positions for culture chambers) is open or transparent (e.g., to facilitate imaging, liquid introduction, cell addition), as shown in FIG. 7B.

Other components present in some embodiments herein are the chambers (e.g., donor, waste, culture, holding). In some embodiments, such as those shown in FIGS. 5 and 6, the chambers comprise closed bottoms and sides, with open, closed, and/or sealable tops. In some embodiments, the chambers comprise one, two, three, or more (e.g., 1, 2, 3, 4, 5, 6, 7, 8, or more, or ranges therein (e.g., 2 or more)) ports 48 for introduction and removal of fluid from the chambers. In some embodiments, the ports 48 comprise openings to the chambers and a component for connection to the fluidic channels 22 (e.g., tubes, 3D printed microchannels).

In some embodiments, chambers are configured (e.g., sized/shaped) for placement into recesses (or between raised portions) of a bottom plate 30. In some embodiments, chambers fit securely in positions (e.g., predetermined positions) displayed on the bottom plate 30. In other embodiments, chambers are attached to, and/or are part of, the bottom plate 30. In some embodiments, a bottom plate 30 is fabricated (e.g., 3D printed) with chambers displayed on its top surface. In some embodiments, a portion of the components displayed on the bottom plate 30 (e.g., chambers, fluidic channels) are part of the bottom plate 30, while another portion of the components displayed on the bottom plate 30 (e.g., pumps, electronics, controller(s), chambers) fit securely within predetermined (e.g., recessed or raised) positions on the bottom plate 30.

Figure 7C:
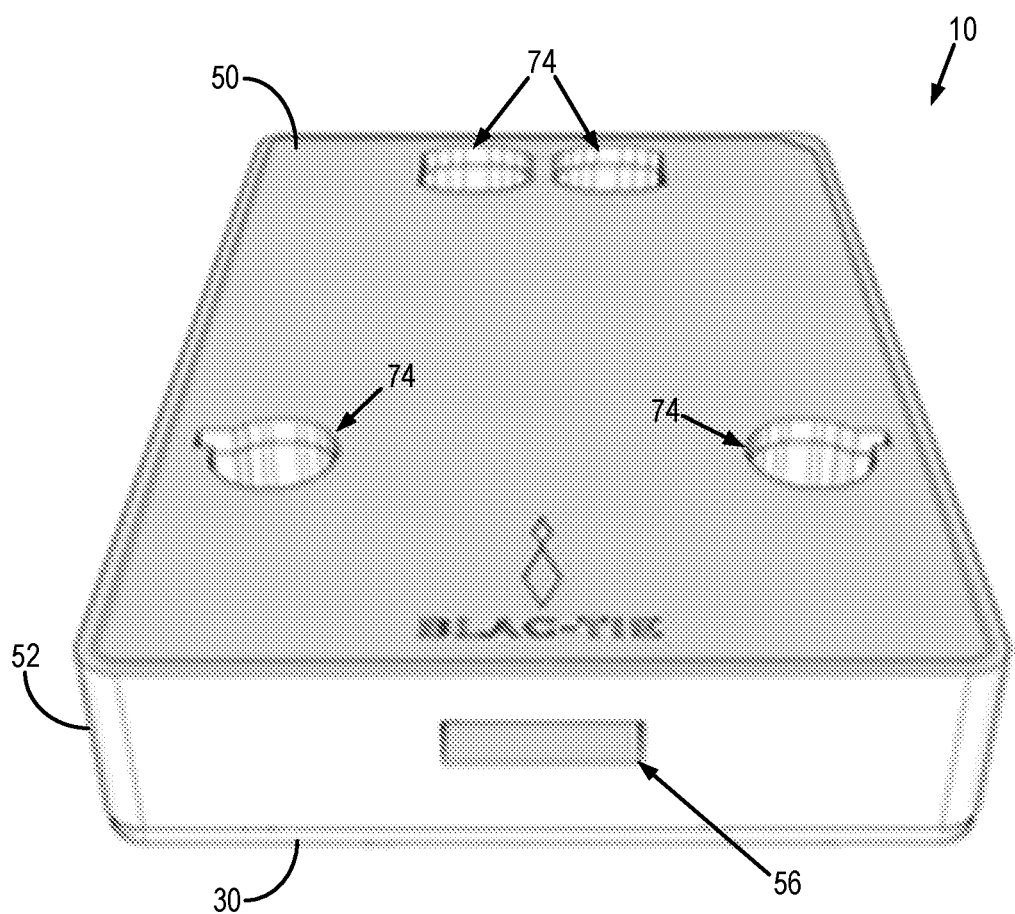
Figure 7D:
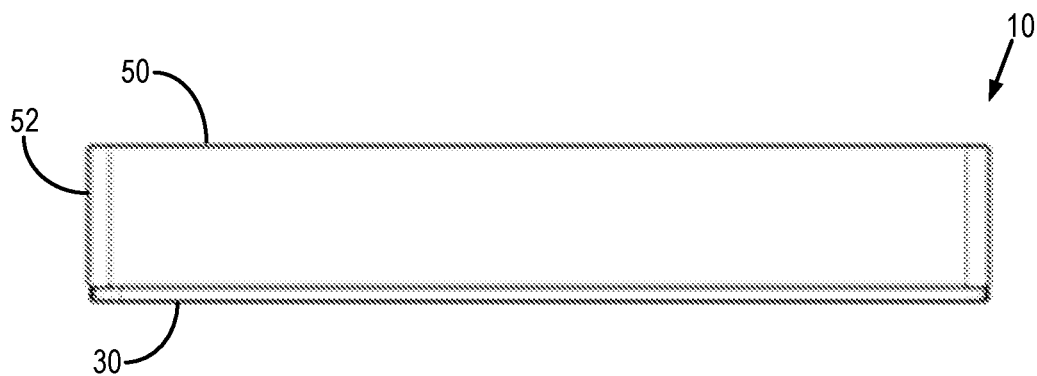

Another component of some embodiments herein is a top plate 50, as shown in FIG. 2. In some embodiments, the top plate 50 comprises a top footprint of a standard microplate. In some embodiments, the underside of the top plate 50 comprises raised portions, recesses, or other features (e.g., columns extending down from the top plate 50) for interfacing with the tops of chambers, the tops of other elements of the tissue culture platform 10 (e.g., pumps, controller, electronics), or a raised portion of the bottom plate 30 (e.g., an exterior ridge rising from the bottom plate 30, interior columns extending up from the bottom plate 30). In some embodiments, the top plate 50 comprises an exterior wall 52 that extends down from its periphery. In some embodiments, the exterior wall 52 engages with the perimeter 54 of the bottom plate 30 to form a closed tissue culture platform 10, as shown in FIGS. 7A-7D. In alternative embodiments, a wall extending up from the perimeter 54 of the bottom plate 30 engages with the perimeter of the top plate 50 to close the tissue culture platform 10. In some embodiments, one or more portions 74 of the top plate 50 (e.g., above positions for culture chambers) is open or transparent (e.g., to facilitate imaging), as shown in FIGS. 7A and 7C. In some embodiments, the exterior wall 52 of the top plate 50 can have formed therein an outlet 56 for receiving a microcontroller 24, or otherwise enabling connection of the microcontroller 24 to an external computer system, that controls the operation of the pumps 20.

In some embodiments described herein, a tissue culture platform 10 comprises a bottom plate 30, top plate 50, and components (e.g., chambers (waste chamber, donor chamber, culture chambers), channels, electronics, pumps, controllers, batteries) that reside between the top plate 50 and the bottom plate 30. In some embodiments, all or a portion of the components are fabricated as part of the top plate 50 and/or the bottom plate 30. In some embodiments, all or a portion of the components are separate from the top plate 50, the bottom plate 30, or both, but reside within predetermined positions (e.g., recesses) on the top plate 50, the bottom plate 30, or both. In some embodiments, the top plate 50, the bottom plate 30, or both, comprise elements for engaging with each other to close (e.g., completely, substantially, partially) the tissue culture platform 10 and/or to secure the components together. In some embodiments, the top plate 50, the bottom plate 30, or both, comprise openings and/or transparent portions to facilitate imaging of the chambers or other portions of the tissue culture platforms 10. In some embodiments, the top plate 50, the bottom plate 30, or both, are transparent.

Thus, some embodiments of the tissue culture platforms 10 described in the present disclosure include a first plate (e.g., bottom plate 30 or top plate 50) and a second plate (e.g., top plate 50 or bottom plate 30) that oppose each other and can be operatively engaged to form an enclosed volume therebetween. For instance, the first plate can have external walls extending from a base of the first plate and these external walls can engage a surface of the second plate to form the enclosed volume between the first plate and the second plate. Preferably, the first plate and the second plate can be removably engaged such that the enclosed volume formed by the first plate and the second plate can be accessed as necessary or desired. As described, a plurality of chambers (e.g., donor chambers, waste chambers, culture chambers) can be coupled to the first plate, the second plate, or both. As also described, a plurality of channels 22 can connect the plurality of chambers. In some embodiments, the channels 22 can be segments of tubing. In some other embodiments, the channels 22 can be microfluidic channels formed in the first plate, the second plate, or both. One or more pumps 20 are also arranged within the enclosed volume and facilitate flow of media between the plurality of chambers. Recesses can be formed in the first plate to couple the plurality of chambers to the first plate. As described, the first plate may be bottom plate 30 or top plate 50.

Figure 5:
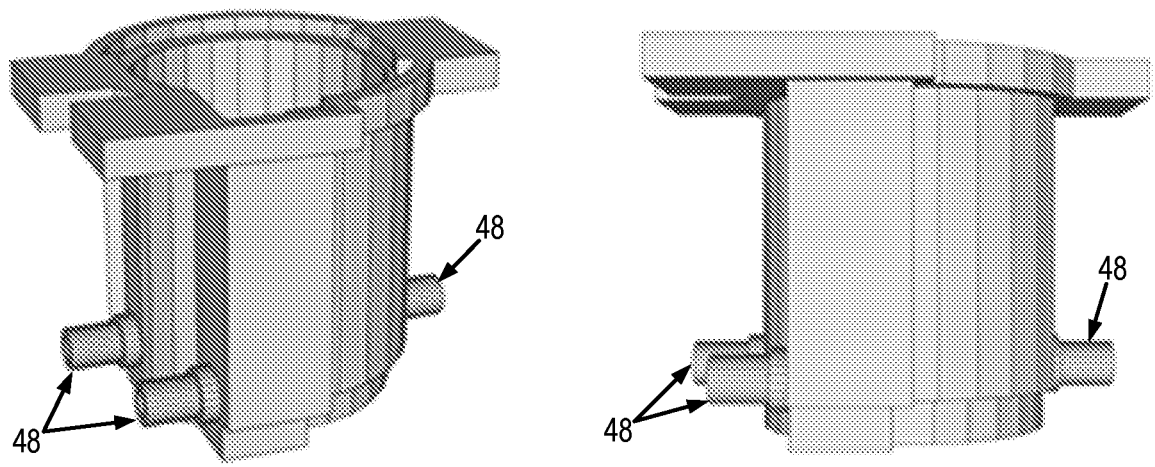
FIG. 5 shows an example of a chamber module design, including three inlet/outlet connections for tubing/fluidic channels, as well as an open reservoir for housing tissue samples.
Figure 6:
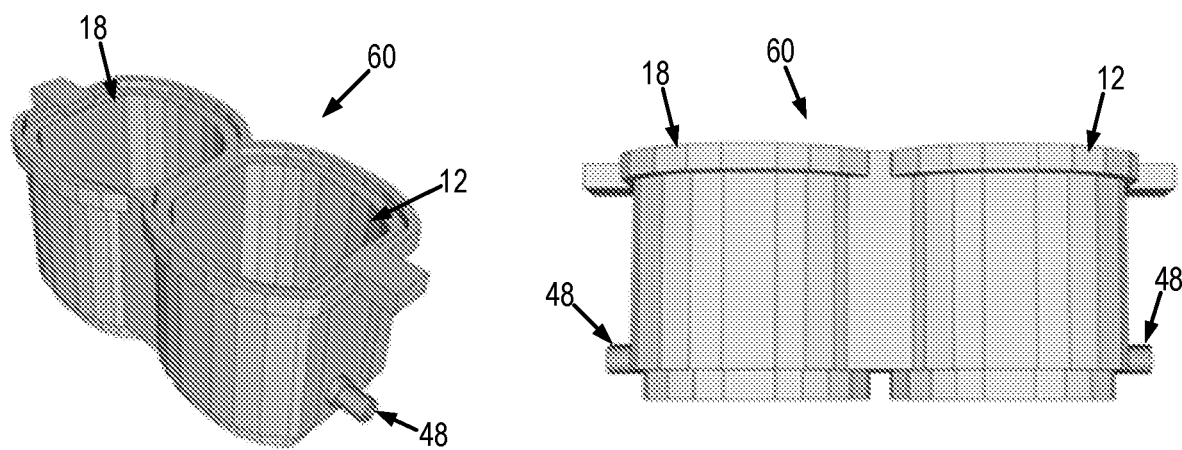
FIG. 6 shows an example of a donor/waste module design, including a single inlet/outlet for both the donor and waste reservoirs for connection to tubing/fluidic channels.

In some embodiments, a variety of different chamber types find use in the tissue culture platforms 10 herein. For example, tissue culture platforms 10 may include a donor chamber 12 that contains liquid (e.g., media) to be provided to a downstream, fluidically-connected chamber or chambers. In some embodiments, tissue culture platforms 10 may include a waste chamber 18 that receives liquid (e.g., spent media) from one or more upstream, fluidically-connected chamber or chambers. In some embodiments, tissue culture platforms 10 comprise multiple donor chambers 12 (e.g., feeding different media to culture chambers), multiple waste chambers 18, or both multiple donor chambers 12 and multiple waste chambers 18. In some embodiments, a chamber is fabricated as a single unit, as shown in FIG. 5. In other embodiments, two or more chambers are fabricated in linked sets, as shown in FIG. 6. As an example, a donor chamber 12 and a waste chamber 18 can be fabricated as a combined donor/waste module 60, in which the donor chamber 12 and the waste chamber 18 are fabricated from a single substrate such that the donor chamber 12 and the waste chamber 18 are separate, isolated volumes, but are physically coupled by the common substrate. For example, in some embodiments, a tissue culture platform 10 comprises a combined donor/waste module and two or more separate culture chambers. Alternative embodiments comprising any combination of combined and separate chambers (e.g., combined culture chambers and separate donor/waste chambers, all separate chambers, one combined unit comprising all chambers) are within the scope herein.

In some embodiments, a donor chamber 12 comprises sufficient media within it to supply the culture chambers (e.g., first culture chamber 14 and second culture chamber 16) and flow for a desired experiment. In other embodiments, the donor chamber 12 is replenished with media. In some embodiments, a donor chamber 12 comprises a port or other opening (e.g., removable lid that can be accessed through the top of the platform) for refilling the donor chamber 12 with media. In other embodiments, a donor chamber 12 comprises a fluid connection (e.g., tubing) to an external media source. In some embodiments, a donor chamber 12 is refilled at discrete time points (e.g., during an experiment). In other embodiments, a donor chamber 12 is continuously refilled via connection to an external media source. In still other embodiments, a tissue culture platform 10 lacks an internal donor chamber and the culture chambers (e.g., first culture chamber 14 and second culture chamber 16) are fed media from an external media source (e.g., donor chamber that is external to the tissue culture platform 10).

In some embodiments, a waste chamber 18 comprises sufficient internal volume to contain the outflow from a desired experiment. In other embodiments, the waste chamber 18 is emptied during an experiment. In some embodiments, a waste chamber 18 comprises a port or other opening (e.g., removable lid that can be accessed through the top of the tissue culture platform 10) for emptying the waste chamber 18. In other embodiments, a waste chamber 18 comprises a fluid connection (e.g., tubing) to an external waste depository. In some embodiments, a waste chamber 18 is emptied at discrete time points (e.g., during an experiment). In other embodiments, a waste chamber 18 is continuously emptied via connection to a waste container. In still other embodiments, a tissue culture platform 10 lacks an internal waste chamber and the waste media empties to an external container.

In some embodiments, chambers are connected via tubing (e.g., tubing with an internal diameter of $3/16$ inch, $5/32$ inch, $1/8$ inch, $3/32$ inch, $1/16$ inch, $1/32$ inch, $1/64$ inch, or ranges therebetween) or channels (e.g. 3D printed channels). In some embodiments, chambers comprise one or more ports (e.g., 1 port, 2 ports, 3 ports, 4 ports, 5 ports, 6 ports, 7 ports, 8 ports, or more, or ranges therebetween (e.g., 1-3 ports)). In some embodiments, ports are inlets. In some embodiments, ports are outlets. In some embodiments, ports function as either/both inlet and outlet. In some embodiments, ports comprise an opening in the chamber. In some embodiments, ports comprise an element on a chamber for attachment to tubing and/or channels, such as the ports 48 shown in FIGS. 5 and 6. In some embodiments, donor chambers 12 and waste chambers 18 contain a single port for fluid flow out of or into the chambers, respectively. In some embodiments, culture chambers comprise at least two (e.g., 2, 3, 4, etc.) ports for connection to donor chamber(s), waste chamber(s), and/or other culture chambers.

In some embodiments, fluid is driven between chambers using one or more (e.g., 1, 2, 3, 4, 5, 6, 7, 8, or more, or ranges therebetween) pumps 20 (e.g., piezoelectric micropumps (e.g., mp6 piezoelectric micropumps)), one or more (e.g., 1, 2, 3, 4, 5, 6, 7, 8, or more, or ranges therebetween) drivers 58 (e.g., mp6-OEM drivers), and a microcontroller 24 (e.g., Teensy 3.2 microcontroller). In some embodiments, fluid is driven through tubing/channels 22 using piezoelectric micropumps connected to drivers 58 that are connected and controlled by a microcontroller 24. In some embodiments, the microcontroller 24 is programmed (e.g., via a coding interface (e.g., Arduino coding interface)) to produce desired pump flow rates and timing of flow. For an example of a two-tissue system, an example of a pump/flow scheme is depicted in FIG. 1. In such embodiments, four on-board pumps direct the flow of the system from donor chamber 12, through the two culture chambers (first culture chamber 14 and second culture chamber 16), and into the waste chamber 18. A first pump 20 is programmed to pump media from the donor chamber 12 to the first culture chamber 14. A second pump 20 then pumps media from the first culture chamber 14 to the second culture chamber 16. Media is then either pumped back to the first culture chamber 14 via a third pump 20 if recirculation is desired/required, or media is pumped to the waste chamber 18 for collection via a fourth pump 20.

In some embodiments, components (e.g., chambers, tubing/channels, ports, pumps) that come in contact with the media and/or tissues are autoclave-compatible. In some embodiments, such a system can is used to culture tissues in a functionally-coupled manner for experiments on the scale of hours (e.g., 1 hour, 2 hours, 4 hours, 6 hours, 8 hours, 10 hours, 12 hours, 16 hours, 20 hours, 24 hours, or more, or ranges therebetween), days (e.g., 1 day, 2 days, 3 days, 4 days, 5 days, 6 days, 7 days, or more or ranges therebetween), or weeks (e.g., 1 week, 2 weeks, 3 weeks, 4 weeks, 5 weeks, 6 weeks, 8 weeks, 12 weeks, 16 weeks, 20 weeks, or more, or ranges therebetween), for example, for the purpose of drug discovery, toxicology, or basic science applications.

In some embodiments, provided herein is a tissue culture platform 10 that includes a single-platform (e.g., with multiple sub-components) culture system comprised of multiple culture subsystems (e.g., each confined to a single culture chamber), wherein each of the culture subsystems is in fluid communication (e.g., bidirectional, unidirectional, continuous, with mixing, without mixing) with at least one of the other subsystems, with a donor subsystem, with a waste subsystem, and so on. In some embodiments, the tissue culture platform 10 is designed to provide appropriate culture conditions (e.g., media, temperature) for each culture subsystem.

Figure 14:
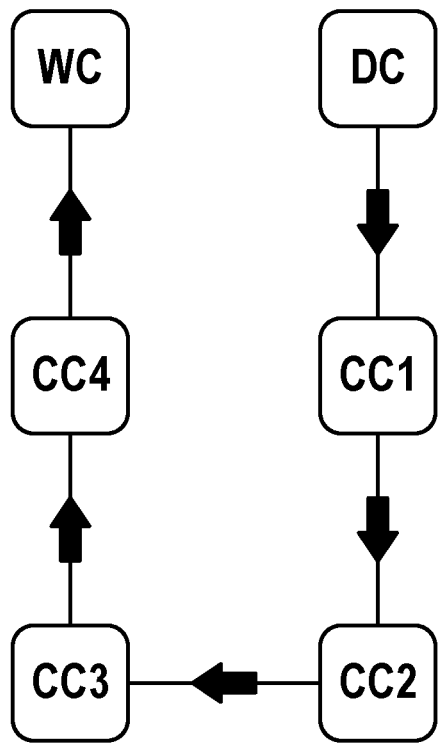
FIG. 14 shows a schematic depicting an example arrangement/connectivity of a donor chamber, four culture chambers, waste chamber and pump(s), demonstrating in-series connectivity of the six chambers.
Figure 15:
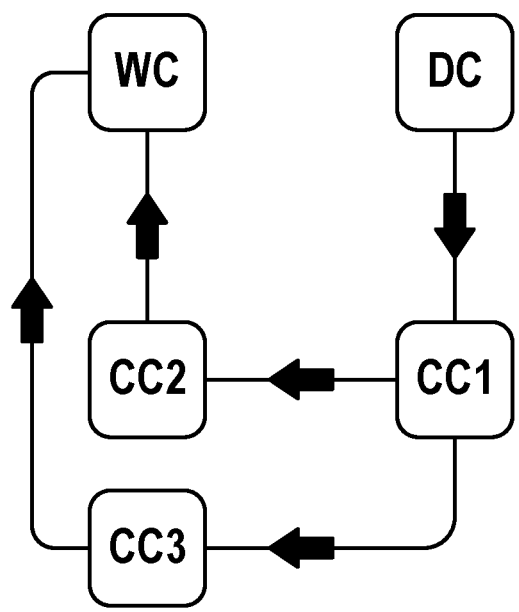
FIG. 15 shows a schematic depicting an example arrangement/connectivity of a donor chamber, three culture chambers, waste chamber and pump(s), demonstrating in-series connectivity of donor chamber to the first culture chamber, parallel connectivity of the first culture chamber to the second and third culture chambers, and parallel connectivity of the second and third culture chambers to the waste chamber.

In some embodiments, a tissue culture platform 10 comprises multiple culture subsystems in fluid communication (e.g., bidirectional, unidirectional, continuous, with mixing, without mixing). For example, unidirectional fluid communication allows downstream cell/tissue types to respond to factors secreted by upstream cell/tissue types in real time. Such a tissue culture platform 10 mimics the dynamic in vivo systems and communication between tissue types that are present in whole organisms. In some embodiments, subsystems (e.g., culture chambers) are connected in series (e.g., one subsystem upstream from a second subsystem) (FIG. 14). In other embodiments, two or more subsystems are connected in parallel (e.g., two or more subsystems downstream and upstream from the same subsystems) (FIG. 15). In some embodiments, two or more subsystems are connected in semi-parallel (e.g., downstream or upstream from the same subsystems, but in series with one or more other subsystems). Any suitable configurations and connectivity of chambers for multiple subsystems are within the scope of the platforms herein.

In some embodiments, dynamic culture (e.g., continuous and/or regulated flow into and/or out of a culture chamber) allows for the transfer of factors from one culture subsystem to another, thereby recapitulating the transfer of factors within complex body systems. Multiple static cultures in which the necessary factors are added by a user or automated system are translated into dynamic systems in which the cells/tissues are able to communicate as they do in vivo, with real-time transfer (e.g., downstream delivery) of hormones and other factors between tissues.

Figure 12A:
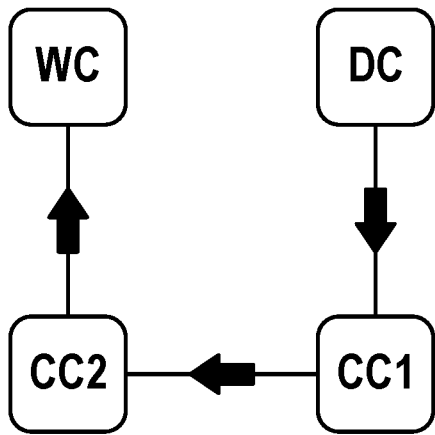
FIGS. 12A-12D show schematics depicting an example arrangement/connectivity of a donor chamber, two culture chambers, waste chamber and pump(s), demonstrating multiple pump arrangements to drive unidirectional flow through the system of chambers.
Figure 12B:
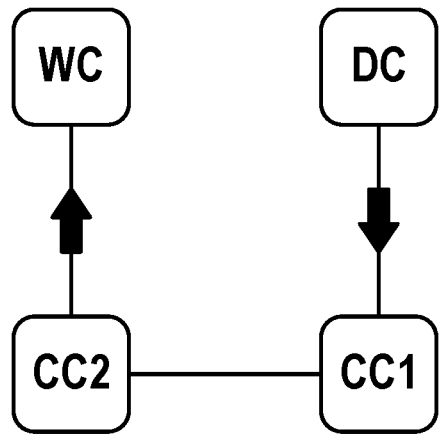
Figure 12C:
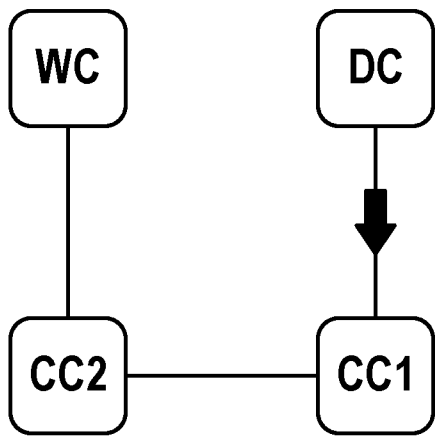
Figure 12D:
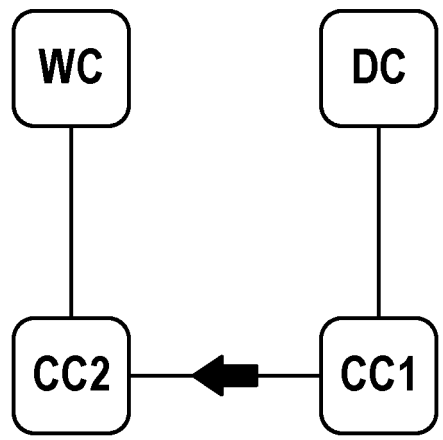

In some embodiments, flow between chambers/culture subsystems is maintained/regulated by pumps. In some embodiments, each connection of two chambers comprises a pump to maintain/regulate from between those two chambers (FIG. 12A). In some embodiments, the connection of two chambers comprises a pump to maintain/regulate from between those two chambers, but the flow between other chambers is passive and/or maintained by pumps upstream and/or downstream of that connection (FIGS. 12B-D).

Figure 13A:
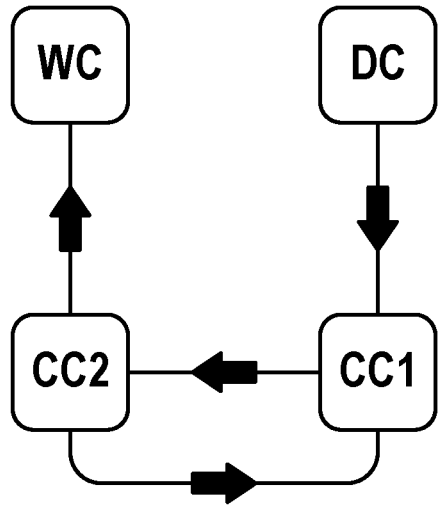
FIGS. 13A and 13B show a schematic depicting an example arrangement/connectivity of a donor chamber, two culture chambers, waste chamber and pump(s), demonstrating unidirectional flow from the donor chamber to the first culture chamber, unidirectional flow from the second culture chamber to the waste chamber, and optional circulating flow ("on" in FIG. 13A and "off" in FIG. 13B) between the first and second culture chambers.
Figure 13B:
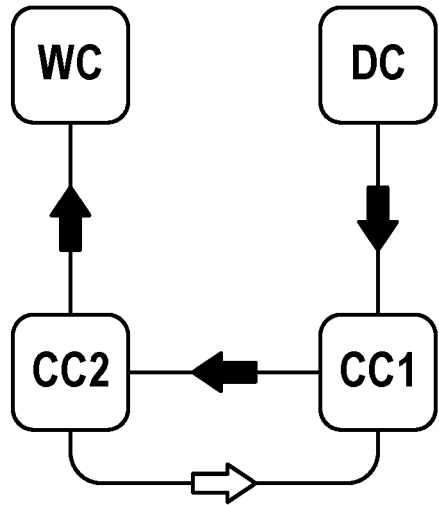

In some embodiments, flow between chambers is passive (e.g., not facilitated by a pump). In some embodiments, unidirectional flow is facilitated by a pump. In some embodiments, circulating flow between chambers may be facilitated by multiple pathways between two chambers (FIG. 13A); in such embodiments, circulating and unidirectional flow may be regulated by increasing/decreasing the relative flow rates of the forward and reverse flow pumps (FIG. 13B).

In some embodiments, the pumps 20 of the tissue culture platforms 10 herein are piezoelectric pumps. In some embodiments, all or a portion of the pumps 20 of the tissue culture platforms 10 herein are electromagnetic actuation-based pumps, pneumatic actuation-based pumps, peristaltic pumps, centrifugal pumps, impedance pumps, and so on. In some embodiments, other techniques for facilitating flow (e.g., between chambers) can be used, including gravity-driven flow, wicking, capillary action, and so on.

In some embodiments, the contained tissue culture platforms 10 described herein permit cells/tissues to be maintained in vitro, under conditions that replicate to those found in vivo. Parameters accurately simulated by the tissue culture platforms 10 described in the present disclosure include, for example, interactions between cells, liquid residence time, liquid to cell ratios, relative size, metabolism by cells, shear stress, and the like. In some embodiments, tissue culture platforms 10 herein mimic the natural state of cells, and/or the predictive value of assays performed therewith. In some embodiments, a network of channels 22 (e.g., tubing and/or microfluidic channels) connect segregated, discrete chambers (e.g., donor, waste, multiple culture chambers). In some embodiments, chamber geometry and connectivity is designed to provide cellular interactions, liquid flow, and liquid residence parameters that correlate with those found for the corresponding cells, tissues, or organs in vivo.

In some embodiments, appropriate chambers are selected for containing cells/tissues and media in the various culturing subsystems. In some embodiments, chambers are designed/selected based upon the type of cell/tissue, and the type of culture (e.g., cell monolayer, explant, spheroid, 3D-printed scaffold). In some embodiments, chambers are vessels of any suitable shape (e.g., cylindrical, box, cube) with one or more ports. In some embodiments, chambers comprise geometries that are optimized to facilitate a particular type of cell culture. For example, chambers may comprise a flat or concave bottom. Chambers may comprise multiple wells.

In some embodiments, a chamber is divided by one or more permeable dividers (e.g., membranes). In such embodiments, cells may be contained within a permeable compartment within a chamber to constrain the cells (e.g., for aggregate or spheroid formation), to prevent outflow of cells, and so on.

In some embodiments, chambers comprise permeable supports (e.g., TRANSWELL-like chambers). In a permeable support, cells are confined to one portion of the chamber, but media, nutrients, hormones, reagents, and so on, may pass beyond the permeable support into a second portion of the chamber. For example, a permeable-support chamber may comprise a flat-bottomed, open-topped, lower compartment with impermeable bottom and sides, and an upper compartment with a microporous membrane (or other permeable surface) which forms the bottom of the upper compartment. The permeable support chamber may have a closed top or a removable lid. In use, cells (e.g., a first type of cells) are placed on the upper surface of the microporous membrane within the upper compartment. The upper compartment is inserted into the lower compartment. Due to the permeability of the support, media, nutrients, factors, and so on, are able to traverse the membrane, but the cells cannot. In some embodiments, cells may also be placed in the lower chamber (e.g., a second type of cells). Other multi-chamber culture systems (e.g., two chambers, three chambers, four chambers, or more) may find use in embodiments described herein. Divisions between chambers may be permeable, semipermeable (e.g., with a particular molecular weight cutoff (e.g., permeable to small molecules, but not proteins), or impermeable.

In some embodiments, chamber ports are positioned on the chambers to allow the movement of media, nutrients, soluble factors, proteins, hormones, etc., but not the cells within the chambers. In some embodiments, ports comprise filters, membranes, or other selectively permeable materials to allow the transfer of media between chambers, but to prevent the transfer of cells/tissues outside of the desired culture subsystem.

In some embodiments, platforms comprise on-board data acquisition components and/or systems. Such components/systems provide for real-time monitoring of cell/growth and/or culture conditions in one or more of the culture subsystems. On-board data acquisition components/systems may comprise: fiber optics, lenses, cameras, and so on (e.g., for optical monitoring within the platform); probes, microparticles, antibodies, and so on (e.g., to detect the presence/absence/level of one or more factors in one or more of the culture subsystems); thermometer (s), pH monitors, and so on (e.g., to monitor media conditions); and other suitable data acquisition components, systems, or both. On-board data acquisition components/systems allow for real-time monitoring of the cultures contained within the closed tissue culture platform 10.

In some embodiments, tissue culture platforms 10 comprise on-board heating and/or cooling elements to provide optimal temperatures for culture. In some embodiments, tissue culture platforms 10 comprise on-board thermometers and/or thermostats. In some embodiments, temperature regulation elements are linked to on-board controllers, processors, and so on, and desired temperatures may be changed in real-time (e.g., to reflect changes in biological conditions). In some embodiments, the entire tissue culture platform 10, the entire media-containing portion of the tissue culture platform 10 (e.g., chambers, fluidics), all the culture chambers, and so on, are maintained at a single temperature (e.g., by heater). In some embodiments, the temperature of each chamber (e.g., culture chamber) is separately regulated (e.g., separate temperature regulation elements for each chamber (e.g., culture chamber)). In other embodiments, tissue culture platforms 10 do not comprise on-board temperature regulation elements, and the temperature of the tissue culture platform 10 is regulated externally. In still other embodiments, tissue culture platforms 10 comprise on-board temperature regulation elements for fine-tuning temperature differences between portions of the tissue culture platform 10 (e.g., differences in temperature between different culture subsystems), but the overall temperature of the tissue culture platform 10 is regulated externally.

In some embodiments, all components for maintaining, regulating, facilitating, and/or monitoring, the flow, culture conditions, and so on, of the various subsystems are contained on board the tissue culture platforms 10 described herein. In other embodiments, one or more off-board components and/or systems are used for maintaining, regulating, facilitating, and/or monitoring, the flow, culture conditions, and so on, of the various subsystems are contained on board the tissue culture platforms 10 described herein. Components and/or functions that may be housed off-board include, for example, temperature control elements, optics (e.g., camera(s), microscope, fluorimeter) for monitoring conditions in chambers (e.g., through transparent walls of chambers), batteries, user interface and/or controller(s) (e.g., connected wirelessly and/or by a physical connection to on-board electronic components, battery or other power source, media reservoir(s)). Other components described herein may also be located off-board in certain embodiments. In other embodiments, the aforementioned components are located on-board.

In some embodiments, the tissue culture platforms 10 and components thereof comprise suitable materials to facilitate the desired functions thereof. Materials may be selected on the basis of porosity, permeability, weight, cost, sterilizability, 3D printability, reactivity, thermal transfer, transparency/opacity, and so on. Suitable materials include plastics, resins, glass, metals, films, membranes, and so on. In some embodiments, components of the tissue culture platforms 10 herein (e.g., top and/or bottom plates, chambers, channels/tubing, pumps, electronics, controllers, etc.) comprise: one or more plastics including but not limited to Bakelite, neoprene, nylon, PVC, polystyrene, polyurethane, polyacrylonitrile, PVB, silicone, rubber, polyamide, synthetic rubber, vulcanized rubber, acrylic, polyethylene, polypropylene, polysulfone, polyethylene terephthalate, polytetrafluoroethylene, gore-tex, polycarbonate, etc.; non-plastic components, such as glass, textiles (e.g., from animal, plant, mineral, and/or synthetic sources), etc.; TEFLON, HDPE, nylon, PEEK, PTFE, and/or PEBAX; or other suitable materials. In some embodiments, components of the tissue culture platforms 10 herein (e.g., top and/or bottom plates, chambers, channels/tubing, pumps, electronics, controllers, etc.) comprise: one or more metals, including but not limited to aluminum, antimony, boron, cadmium, cesium, chromium, cobalt, copper, gold, iron, lead, lithium, manganese, mercury, molybdenum, nickel, platinum, palladium, rhodium, silver, tin, titanium, tungsten, vanadium, zinc, and alloys thereof.

In some embodiments, one or more surfaces of a component of the tissue culture platforms 10 herein are coated to impart one or more desired characteristics and/or functionalities. For example, hydrophobic coating may be used on one or more surfaces of a component. Suitable hydrophobic coatings include paralyene, polytetrafluoroethylene, and so on.

In embodiments, surfaces of the chambers, channels, and so on, may be formed from non-adherent materials or may be coated with non-adherent materials to form a non-adherent surface. Example non-adherent materials include perfluorinated polymers, olefins, or like polymers or mixtures thereof. Other examples include agarose, non-ionic hydrogels such as polyacrylamides, polyethers such as polyethylene oxide, and polyols such as polyvinyl alcohol, or like materials or mixtures thereof.

In some embodiments, the plates, chambers, channels, and/or other components of the tissue culture platforms 10 herein are produced by known fabrication techniques, such as laser machining, injection molding, 3D printing, hot embossing, additive manufacturing, lithography, milling, and so on. The tissue culture platforms 10 and/or components thereof are not limited by the techniques for fabrication/assembly thereof.

In some embodiments, the tissue culture platforms 10 herein find use in the simultaneous culture of two or more cell/tissues in separate culture chambers, while allowing communication between chambers, via the transfer (e.g., unidirectional, bidirectional, circulating) of sufficiently small or soluble agents and reagents (e.g., media, buffer, small molecules, hormones, peptides, proteins) between the chambers. In some embodiments, the communication (e.g., fluid transfer) between the culture chambers allows for mimicry of in vivo and/or whole organism conditions. In some embodiments, any combination of cell/tissue types my find use in embodiments herein. In some embodiments, systems are provided comprising a tissue culture platform 10 described herein, two or more cell/tissue types in culture, and appropriate media. In some embodiments, the cells/ tissues cultured in the tissue culture platforms 10 herein are related and/or interact in a whole-animal context. In some embodiments, different cells types of a tissue, organ, body system, and so on, are cultured in the tissue culture platforms 10 herein to replicate the in vivo conditions of the respective tissue, organ, body system, and so on. For example, multiple cell/tissue types may be cultured in the platforms herein to replicate, for example, a reproductive system, cardiac system, nervous system, circulatory system, respiratory system, digestive system, urinary or excretory system, integumentary system, muscle system, skeletal system, endocrine system, immune system, a disease state (e.g., cancer), and/or combinations or portions thereof. In particular embodiments, multiple cells/tissues of the female reproductive tract (See, e.g., U.S. Pat. No. 9,695,399; incorporated by reference in its entirety) are cultured in the tissue culture platforms 10 herein. The tissue culture platforms 10 herein are similarly useful with other systems.

Figure 8:
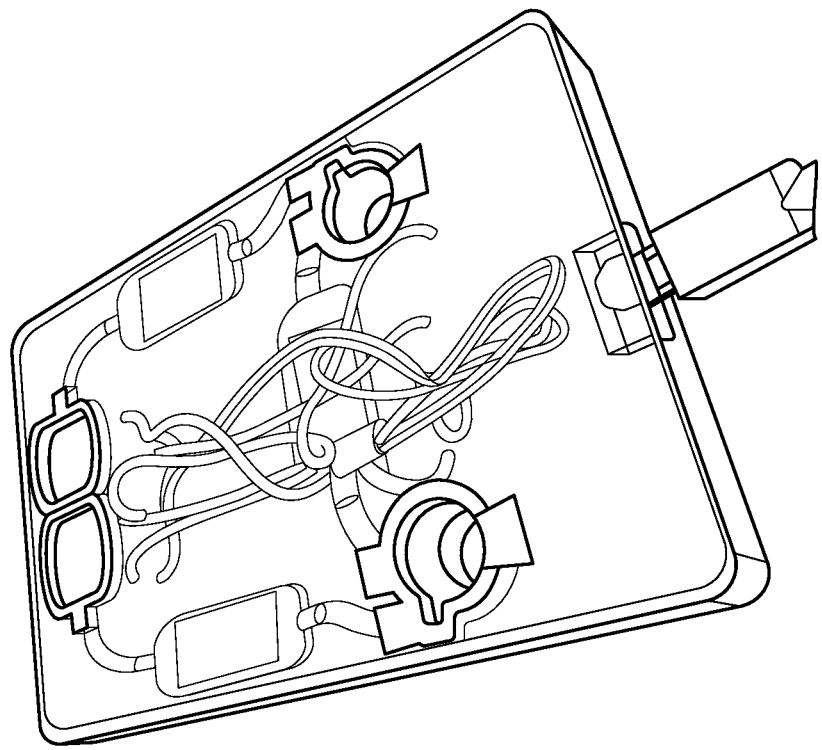
FIG. 8 is an image of an example tissue culture platform assembled within sterile hood with transwell inserts within each chamber and media being pumped through the tissue culture platform system (external power source used).
Figure 8:
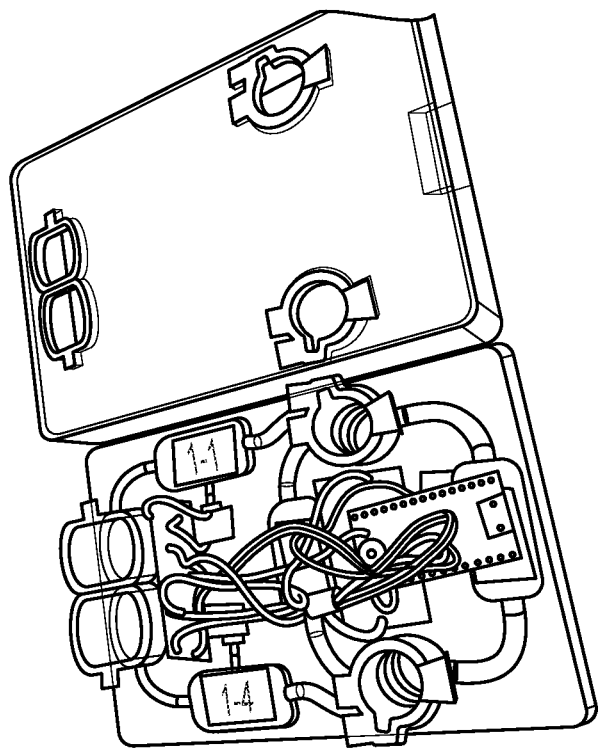
Figure 9:
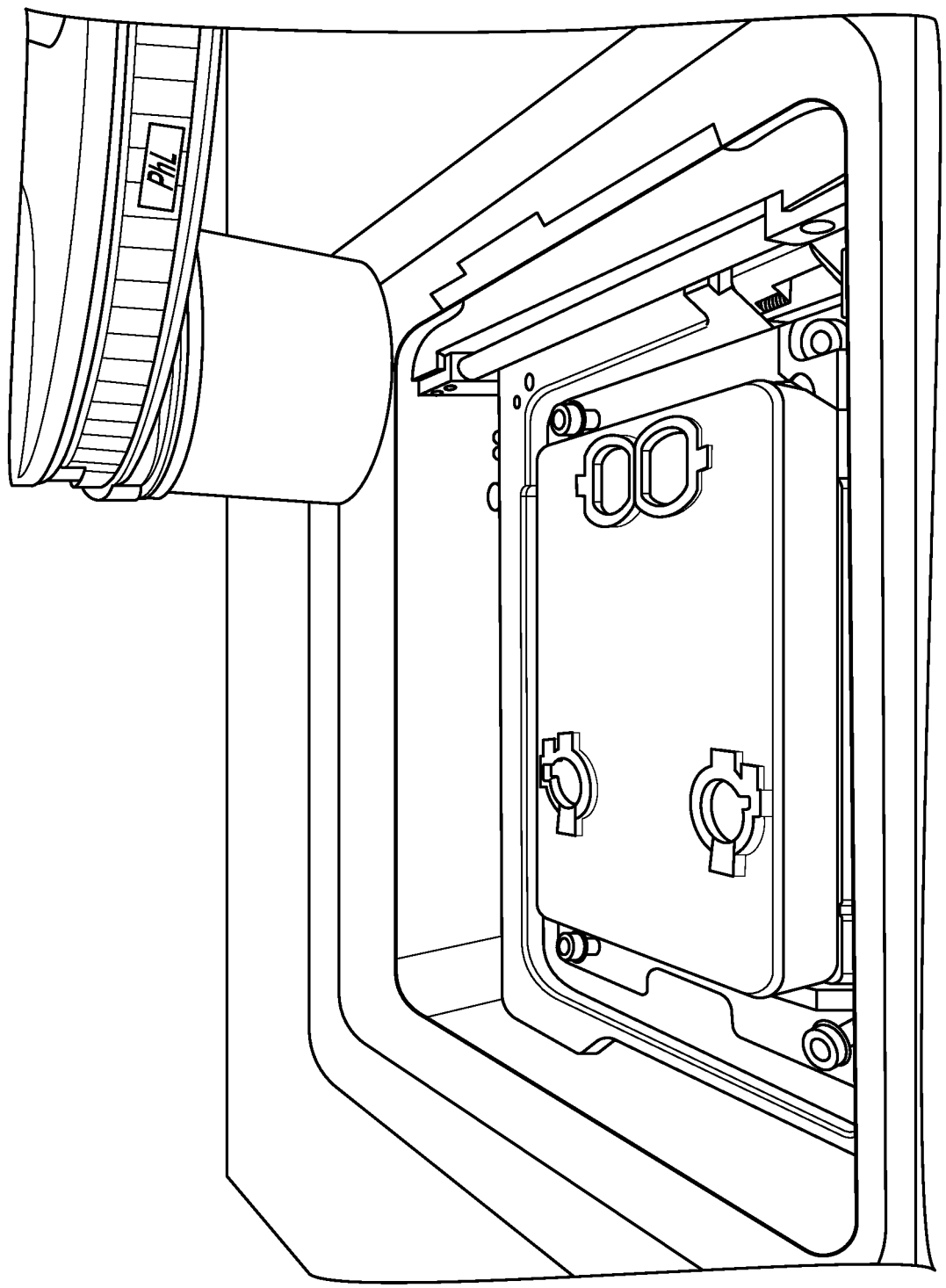
FIG. 9 shows an image of an example tissue culture platform within an automated imaging instrument, illustrating size compatibility with lab automation hardware.

An example of a tissue culture platform 10 in accordance with some embodiments described in the present disclosure is shown in FIG. 8. In this example, the tissue culture platform 10 is assembled within sterile hood with transwell inserts within each chamber. Media is pumped through the tissue culture platform 10 using an external power source to power pumps. FIG. 9 shows an image of the tissue culture platform shown in FIG. 8 positioned within an automated imaging instrument, illustrating size compatibility with lab automation hardware.

Figure 10:
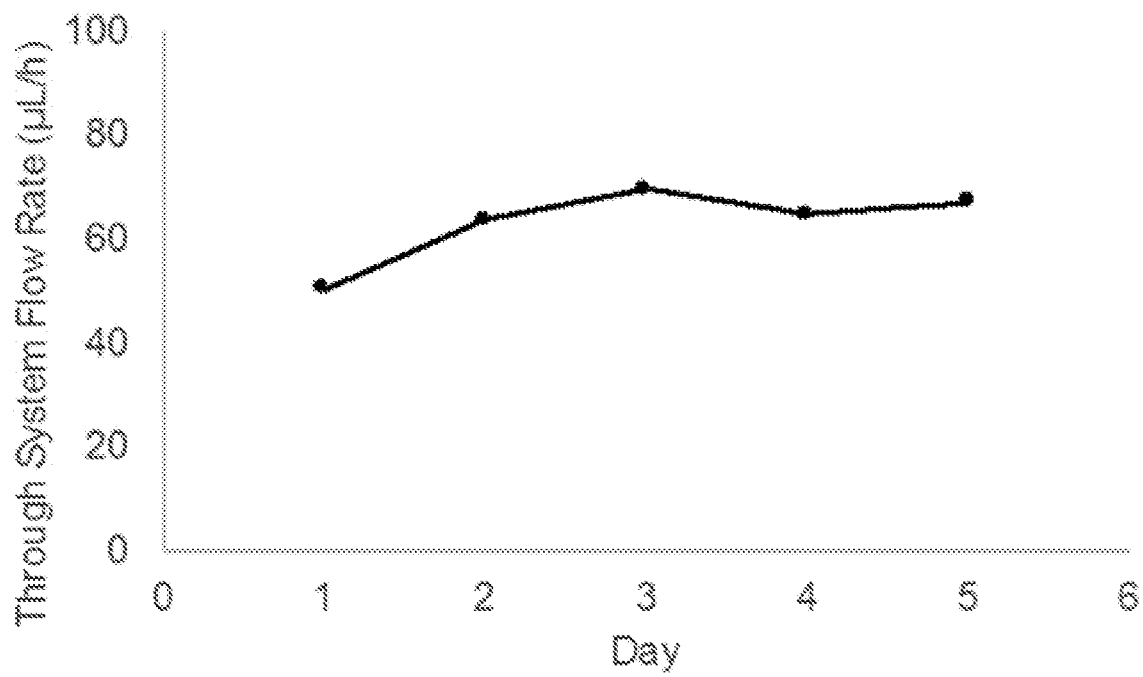
FIG. 10 is a graph depicting the through-system flow rate from an example of a tissue culture platform operated within sterile incubator, illustrating stable flow rates at culture conditions.

In an example study, through-system flow rate was measured for an example construction of a tissue culture platform according to embodiments described in the present disclosure. A graph depicting the measured through-system flow rate from an example of a tissue culture platform operated within a sterile incubator is shown in FIG. 10. The measurements illustrate that stable flow rates at culture conditions can be established using the tissue culture platforms described in the present disclosure.

Figure 11:
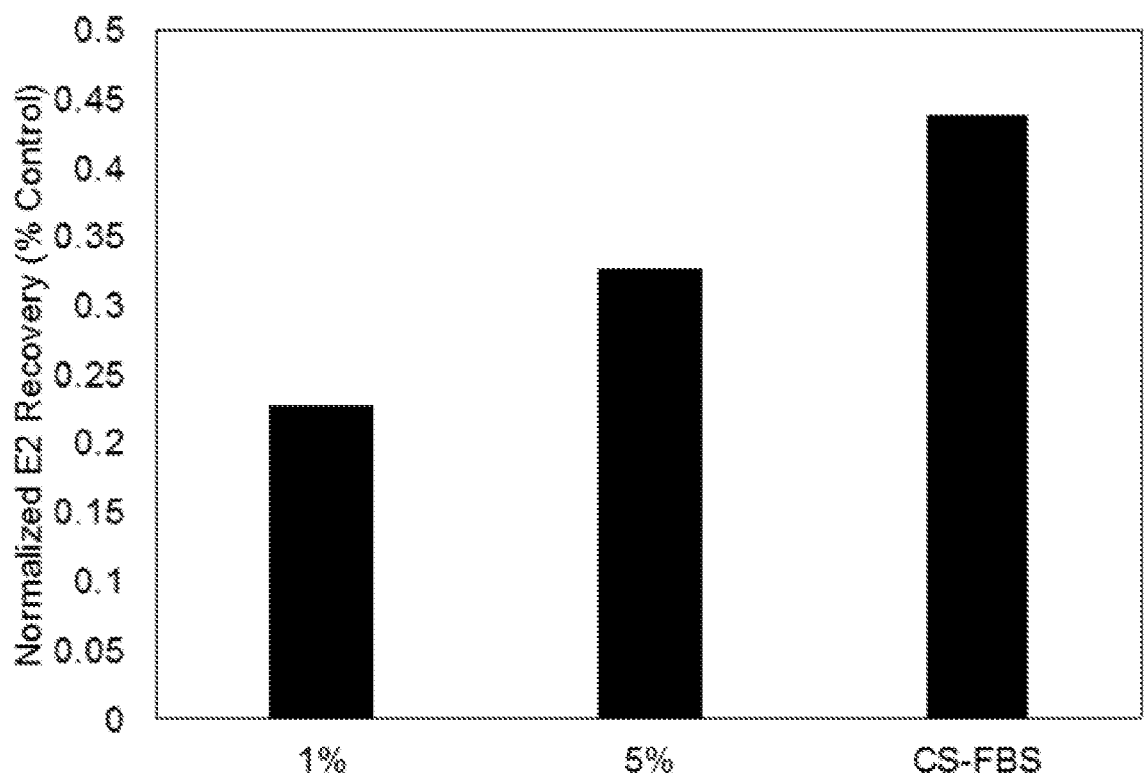
FIG. 11 is a graph depicting estradiol recovery from media incubated within Dental SG wells pre-conditioned with either 1% F108, 5% F108, or charcoal-stripped fetal bovine serum for 24 h normalized with respect to a control condition.

In another example study, estradiol recovery was measured from media incubated within culture chambers of an example tissue culture platform constructed according to embodiments described in the present disclosure. The culture chambers were composed of a Dental SG resin and were pre-conditioned with either 1% F108, 5% F108, or charcoal-stripped fetal bovine serum for 24 h. A graph depicting the measured estradiol recovery, normalized with respect to a control condition, is shown in FIG. 11.

The present disclosure has described one or more preferred embodiments, and it should be appreciated that many equivalents, alternatives, variations, and modifications, aside from those expressly stated, are possible and within the scope of the invention.

The invention claimed is:

1. A tissue culture platform having standard microplate dimensions and comprising:
    a first plate;
    a second plate opposed to and engaging the first plate to form an enclosed volume therebetween;
    a plurality of chambers coupled to at least one of the first plate or the second plate and enclosed within the enclosed volume;
    a plurality of channels enclosed within the enclosed volume and connecting the plurality of chambers to allow flow of media therebetween; and
    at least one pump enclosed within the enclosed volume, wherein the at least one pump facilitates the flow of media between the plurality of chambers and regulates a directionality of the flow of media between the plurality of chambers;
    wherein the plurality of chambers are selectively connected by the plurality of channels to create a desired media flow-path through and between the plurality of chambers, thereby providing for dynamic tissue culture conditions between the plurality of chambers;
    wherein the plurality of chambers comprises:
    a plurality of culture chambers, each of the culture chambers configured to contain a volume of culture media and cells, wherein each culture chamber comprises an inlet port and an outlet port each configured to allow the flow of media between the culture chambers while preventing movement of the cells between the culture chambers;
    at least one donor chamber configured to contain a volume of culture media, wherein the at least one donor chamber comprises an outlet port configured to allow the flow of media from the at least one donor chamber to one or more of the plurality of culture chambers via one or more of the plurality of channels and facilitated by the at least one pump;
    at least one waste chamber configured to contain a volume of culture media, wherein the at least one waste chamber comprises an inlet port configured to receive media from one or more of the plurality of culture chambers via one or more of the plurality of channels and facilitated by the at least one pump
    wherein the at least one donor chamber and the at least one waste chamber are not in direct fluid connection with each other;
    wherein the plurality of channels comprises at least four channels;
    wherein the at least one donor chamber is connected to at least one of the culture chambers via the plurality of channels, the plurality culture chambers are connected to each other via the plurality of channels, and at least one of the plurality of culture chambers is connected to the at least one waste chamber via the plurality of channels in order to create the desired media flow-path through and between the plurality of chambers; and
    wherein the at least one pump facilitates the directionality of flow through the at least four channels such that unidirectional flow is provided from the at least one donor chamber to the plurality of culture chambers, one of bidirectional flow or mixing of media is provided between the plurality of culture chambers, and unidirectional flow is provided from the plurality of culture chambers to the at least one waste chamber.

2. The tissue culture platform of claim 1, wherein the first plate comprises exterior walls extending away from a base of the first plate such that the exterior walls engage with the second plate to form the enclosed volume.

3. The tissue culture platform of claim 1, wherein the first plate comprises a plurality of recesses formed therein that couple the plurality of chambers to the first plate.

4. The tissue culture platform of claim 1, wherein the plurality of channels comprise sections of tubing.

5. The tissue culture platform of claim 1, wherein the plurality of channels comprise microfluidic channels formed in the first plate.

6. The tissue culture platform of claim 1, wherein the at least one pump is positioned along one of the plurality of channels connecting a pair of the plurality of chambers.

7. The tissue culture platform of claim 6, wherein the at least one pump facilitates unidirectional flow between the pair of the plurality of chambers.

8. The tissue culture platform of claim 1, further comprising a microcontroller that is electronically linked to the at least one pump and controls the flow of media through the plurality of chambers, the plurality of channels, and the at least one pump.

9. The tissue culture platform of claim 8, further comprising a power source connected to at least one of the microcontroller or the at least one pump.

10. The tissue culture platform of claim 9, wherein the power source is a battery enclosed within the enclosed volume.

11. The tissue culture platform of claim 9, wherein the power source is located externally to the enclosed volume.

12. The tissue culture platform of claim 1, wherein at least one of the first plate or the second plate comprises one or more openings to allow access to the enclosed volume when the first plate is engaged with the second plate.

13. The tissue culture platform of claim 1, wherein at least one of the first plate or the second plate comprises one or more transparent portions to provide visual access to one or more of the plurality of chambers.

14. The tissue culture platform of claim 13, wherein the visual access allows at least one of quantitative or qualitative assessment of contents of one or more of the plurality of chambers.

15. The tissue culture platform of claim 1, wherein at least two of the plurality of chambers are fabricated as a one-piece unit.

* * * * *